United States Patent [19]

Munford

[11] Patent Number: 5,744,304
[45] Date of Patent: Apr. 28, 1998

[54] INFLAMMATION-INDUCED EXPRESSION OF A RECOMBINANT GENE

[75] Inventor: Robert S. Munford, Dallas, Tex.

[73] Assignee: Board of Regents, The University of Texas System, Austin, Tex.

[21] Appl. No.: 456,103

[22] Filed: May 30, 1995

[51] Int. Cl.$^6$ .................................................. C12Q 1/68
[52] U.S. Cl. ...................... 435/6; 435/172.3; 435/69.1; 514/44
[58] Field of Search ......................... 435/69.1, 240.2, 435/172.3, 6; 514/44

[56] References Cited

U.S. PATENT DOCUMENTS 5,217,870  6/1993  Hession et al. .................. 435/7.24

OTHER PUBLICATIONS

Orkin et al., *Report and Recommendations of the Panel to Access the N/H Investment in Research on Gene Therapy*, N/H, 1995.

Alcorn et al., "Genomic Elements Involved in Transcriptional Regulation of the Rabbit Surfactant Protein–A Gene," *Molecular Endocrinology*, 7(8):1072–1085, 1993.

Baumann and Gauldie, "The Acute Phase Response," *Immunology Today*, 15(2):74–80, 1994.

Casey, "Role of Cytokines in the Pathogenesis of Cardiopulmonary–Induced Multisystem Organ Failure," *Ann. Thorac. Surg.*, 56:592–596, 1993.

Cioffi et al., "Leukocyte Responses to Injury," *Arch Surg.*, 128:1260–1267, Nov. 1993.

Conary et al., "Protection of Rabbit Lungs from Endotoxin Injury by In Vivo Hyperexpression of the Postaglandin G/H Synthase Gene," *J. Clin. Invest.*, 93:1834–1840, Apr. 1994.

Cox et al., "Bovine Herpesvirus 1: Immune Responses in Mice and Cattle Injected with Plasmid DNA," *Journal of Virology*, 67(9):5664–5667, Sep. 1993.

Evans et al., "Protective Effects of a Recombinant Amino–Terminal Fragment of Human Bactericidal/Permeability–Increasing Protein in an Animal Model of Gram–Negative Sepsis," *The Journal of Infectious Diseases*, 171:153–160, 1995.

Fattori et al., "Defective Inflammatory Response in Interleukin 6–Deficient Mice," *J. Exp. Med.*, 180:1243–1250, Oct. 1994.

Hayashi et al., "Expression of a Thyroid Hormone–responsive Recombinant Gene Introduced into Adult Mice Livers by Replication–defective Adenovirus Can Be Regulated by Endogenous Thyroid Hormone Receptor," *The Journal of Biological Chemistry*, 269(39):23872–23875, 1994.

Klein et al., "Interleukin–6 in Human Multiple Myeloma," *Blood*, 85(4):863–872, Feb. 1995.

Kobayashi et al., "Transfer of a Constitutive Viral Promoter—Cystic Fibrosis Transmembrane Conductance Regulator cDNA to Human Epithelial Cells Conveys Resistance to Down–Regulation of cAMP–Regulated Cl Secretion in the Presence of Inflammatory Stimuli," *Nucleic Acids Research*, 22(21):447—4476, 1994.

Kolls et al., "Adenovirus–Mediated Blockade of Tumor Necrosis Factor in Mice Protects Against Endotoxic Shock yet Impairs Pulmonary Host Defense," *The Journal of Infectious Diseases*, 171:570–575, 1995.

Peppel et al., "Prolonged and effective blockade of tumor necrosis factor activity through adenovirus–mediated gene transfer," *Proc. Natl. Acad. Sci. USA*, 91:215–219, 1994.

Kopf et al., Impaired Immune and Acute–Phase Responses in Interluekin–6–Deficient Mice, *Nature*, 368:339–342, Mar. 1994.

Lynn and Cohen, "Adjunctive Therapy for Septic Shock: A Review of Experimental Approaches," *Clinical Infectious Diseases*, 20:143–158, 1995.

Malone et al., "Dexamethasone Enhancement of Gene Expression after Direct Hepatic DNA Injection," *The Journal of Biological Chemistry*, 269(47):29903–29907, Nov. 1994.

McPhaul et al., "The Adenovirus–Medicated Delivery of a Reporter Gene Permits the Assessment of Androgen Receptor Function in Genital Skin Fibroblast Cultures," *The Journal of Biological Chemistry*, 268(35):26063–26066, Dec. 1993.

Munford and Hall, "Detoxification of Bacterial Lipopolysaccharides (Endotoxins) by a Human Neutrophil Enzyme," *Science*, 234:203–205, Oct. 1986.

Rogy et al., "The Role of Bactericidal/Permeability–Increasing Protein in the Treatment of Primate Bacteremia and Septic Shock," *J. Clin. Immunol.*, 14(2):120–133, 1994.

Roessler et al., "Adenoviral–mediated Gene Transfer to Rabbit Synovium In Vivo," *J. Clin. Invest.*, 92:1085–1092, 1993.

Savino et al., "Rational Design of a Receptor Super–Antagonist of Human Interleukin–6," *The EMBO Journal*, 13(24):5863–5870, 1994.

Suffredini, "Current prospects for the treatment of clinical sepsis," *Critical Care Medicine*, 22(7):S12–S18, 1994.

Ulmer et al., "Heterologous Protection Against Influenza by Injection of DNA Encoding a Viral Protein," *Science*, 259:1745–1749, Mar. 1993.

Wang et al., "Gene Inoculation Generates Immune Responses Against Human Immunodeficiency Virus Type 1," *Proc. Natl. Acad. Sci. USA*, 90:4156–4160, May 1993.

Watanabe et al., "Inhibitin of IL–1β–Induced Peripheral Inflammation by Peripheral and Central Administration of Analogs of the Neuropeptide α–MSH," *Brain Research Bulletin*, 32:311–314, 1993.

Yang et al., "Cellular Immunity to Viral Antigens Limits E1–deleted Adenoviruses for Gene Therapy," *Proc. Natl. Acad. Sci. USA*, 91:4407–4411, May 1994.

*Primary Examiner*—James Ketter
*Attorney, Agent, or Firm*—Arnold, White & Durkee

[57] ABSTRACT

The present invention describes methods of controlling and regulating the inflammatory reaction generated in response to various toxins, immunogens, pathogens and autoimmune insults. The method employs a vector that includes an anti-cytokine protein or antibacterial protein gene under the control of a cytokine responsive promoter. In animal models, adenoviral vectors successfully delivered the vectors to hepatic cells and were subsequently shown to respond only to stimulation by induced cytokines.

10 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

AGGATCGATA ATGCAATGCC AAATGTG                                    27

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

TTTTGGATCC AAAAAGGTGG AAGGAATGAA                                 30

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

CTCATCGATA TCCCATGATT TATCACAC    28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

TTTTGGATCC GGGACCCCAG GTGAGTGG    28

INFLAMMATION-INDUCED EXPRESSION OF A RECOMBINANT GENE

BACKGROUND OF THE INVENTION

The United States government has rights in the invention pursuant to grant 92-03654 from the United States Department of Agriculture and grant A118188 from the National Institute of Allergy and Infectious Diseases.

FIELD OF THE INVENTION

The invention relates to methods and compositions useful for prevention or treatment of disease or toxicity-induced inflammation. Recombinant genes that include cytokine-responsive promoters are employed to express heterologous gene products in response to inflammatory stimuli. The invention particularly relates to polypeptide expression that is responsive to inflammation-induced cytokine production.

DESCRIPTION OF RELATED ART

Local and systemic inflammation elicit a wide range of host responses which include fever, hypoglycemia, cachexia, changes in liver plasma protein concentration and in immune system response. Inflammatory response is mediated by several factors, including Interleukin-6 (IL-6), IL-1 and tumor necrosis factor alpha (TNF-α) (Fattori, et al, 1994). Injury for example causes an immune system response in which activated leukocytes produce cytokines and other metabolic products that may act either to the host's benefit or cause systemic inflammation that may depress the function of major organs, remote from the site of the injury (Cioffi, et al, 1993).

There have been efforts to evaluate agents to prevent and control infection and to use antagonists and antibodies to control the overreactions of the host to cytokine action. Unfortunately, the redundancies of cell populations and the complex interactions of cytokines and cytokine-induced products have made it difficult to identify a single agent to control or regulate inflammatory response. Clinical evaluation of putative regulatory agents has therefore been extremely limited.

Inflammatory cytokines (e.g., TNF, IL-1) are critical components of the host defense toward invading microbes; however, high concentrations of cytokines may be deleterious to the host, contributing to organ failure, shock, and death. The release of several inflammatory mediators is implicated in the pathogenesis of sepsis, including not only the cytokines IL-1, IL-6, and TNF but also lipid and arachidonate metabolites, platelet-activating factor and activation of the coagulation cascade (Casey, 1993). One approach to controlling or ameliorating reaction to the deleterious effects of overreaction to an inflammatory response is to administer compounds that suppress or control the causative agents of inflammatory response, e.g., anti-cytokine compounds. Unfortunately, as concluded from the results of several clinical trials (Suffredini, 1994; Lynn, 1995) the determination of optimal dose and timing of exogenously administered anti-cytokine proteins in septic patients is very difficult.

Several studies have been conducted on different anti-cytokine therapies for the treatment of septic shock, including polyclonal antiendotoxin anticore antibodies, monoclonal antiendotoxin antibodies, anti-tumor necrosis factor-α (TNF-α) therapies, and interleukin-1 (IL-1) receptor antagonist. A review of animal and human clinical trials that have tested various anti-cytokine therapies indicates that none of these drugs has improved survival and in some may have had deleterious effects (Suffredini, 1994; Lynn, 1995).

Other approaches have utilized gene therapy methods. For example, using gene transfer vectors in mice (Kolls et al., 1994), researchers constructed a chimeric protein capable of binding and neutralizing tumor necrosis factor (TNF). While the desired effect of producing high levels of constitutively produced lymphotoxin was achieved using this system, it was also reported that the animals were rendered highly susceptible to infection by *Listeria monocytogenes*. These results indicated the potential of producing potentially therapeutically useful polypeptides in vivo; unfortunately, the method may also have increased host susceptibility to opportunistic infection.

A similar approach to developing therapies for rheumatoid arthritis and other inflammatory arthropathies has been reported by Roesster, et al (1993). Synovial lining cells were genetically transfected in mice with recombinant adenoviral vectors containing β-galactosidase gene. It was suggested that directed overexpression of biologically active anti-inflammatory proteins by synovicytes would be a potential therapeutic intervention to prevent the anti-inflammatory cascade. However, the problem of internal control of such overexpression was not addressed.

Conary, et al (1994) have reported constitutive overexpression of prostaglandin synthase in rabbits using DNA/liposome complexes for transfection. The DNA was under the control of a CMV promoter and was found to result in continuous overexpression of the synthase. The DNA was expressed predominantly in the lungs with resultant production of prostaglandin E2 and prostacyclin. Several pulmonary responses to endotoxin were shown to be attenuated. Again, however, the issue of control of overexpression was not addressed.

Unfortunately, the problem of in vivo regulation of exogenously induced vectors is not solved with the use of the viral promoters typically used in vectors proposed for gene therapy. Most gene therapy vectors in current use rely on exogenous viral promoters for expression of recombinant proteins in vivo. The SV40, RSV and CMV early promoters are active in a wide range of tissues, drive high-level constitutive expression, and do not require specific inducing signals. However, these properties may in fact be undesirable. For some therapeutic applications, it will be desirable to restrict expression of a recombinant gene to particular tissues or cells and to vary expression levels in response to physiological conditions. The viral promoters conventionally employed in gene transfer are not always limited to tissue specific induction signals. This underscores the need for in vivo control on an "as needed" basis.

In vitro studies have shown that promoters can remain responsive to appropriate exogenous stimuli when they are transferred into cultured cells using adenoviral vectors (Alcorn et al., 1993; McPhaul et al., 1993). An adenoviral vector containing a thyroid hormone-responsive enhancer was reported to mediate thyroid hormone-inducible recombinant protein expression in vivo (Hayashi et al., 1994). However, this system has inherent limitations including a relatively low degree of inducibility and constitutive expression in response to normal blood levels of thyroid hormone.

A particular need therefore exists to devise methods of regulating or modulating the destructive or pathological overreactivity of the natural immune system. Uncontrolled immune response may result in systemic inflammatory disease and diseases such as rheumatoid and osteoarthritis. Any system that inhibits overstimulation of the inflammatory response should ideally cause little or no interference with the natural immunity of an animal. To control the inflammatory response without inducing immunosuppression, therefore, very low basal (constitutive) expression must be coupled with high-level inducibility in response to circulating inflammatory signals, e.g., cytokines.

SUMMARY OF THE INVENTION

The present invention seeks to overcome these and other drawbacks inherent in the prior art by providing novel methods of controlling the cytokines or other inflammatory mediators produced in a host as a result of local or systemic inflammation. The disclosed methods make possible control of the rate and extent of anti-inflammatory protein, hereinafter "antidote", production in a negative feedback manner. In the absence of inflammation, little or not antidote protein will be produced. When inflammation occurs, antidote protein(s) will be produced according to the intensity of the inflammatory reaction (i.e. in response to circulating inflammatory cytokines or other mediators). Antidote protein production will limit the extent and duration of the inflammatory reaction, avoiding dangerous (toxic) excess. As the inflammatory reaction wanes, antidote protein production will decrease, thereby avoiding prolonged immunosuppression.

The new methods of control of inflammatory response are based on the use of gene vectors. The inventors have demonstrated that promoters for two murine acute phase protein (APP) genes are capable of increasing recombinant protein expression in response to inflammatory stimuli in vivo. It is now possible to regulate gene product expression in direct response to mediators of the inflammatory response in a host.

The methods disclosed are important, e.g., in controlling endogenous production or action of cytokines, compounds that comprise a group of low molecular weight regulatory proteins secreted by white blood cells and other cells in response to certain stimuli. As such, cytokines may be viewed as messengers of the immune system, particularly in consideration of their role in inflammatory response caused by disease and injury. There are numerous cytokines, including interleukins and interferons. Exemplary cytokines include leukemia inhibitory factor, oncostatin M, transforming growth factor $\beta$, IL-1, tumor necrosis factor $\alpha$ and tumor necrosis factor $\beta$.

In certain embodiments the invention may be described as a nucleic acid segment comprising an anti-inflammatory protein gene positioned under the transcriptional control of a promoter responsive to endogenously produced mediators of inflammation, e.g., a cytokine-responsive promoter.

An inflammatory reaction may arise as a response to a range of insults to the host. For example, inflammatory agents include toxins or pathogens such as virus or bacteria. Inflammation may arise from an autoimmune response to the host's own proteins; in reaction to injury; or as an immune response to allergens. Acute inflammation may be serious and result in pathologic consequences. Typically, acute inflammation is exhibited as a systemic response characterized by a rapid alteration in the levels of several plasma proteins. These proteins may include increased ACTH and acute phase proteins such as C-reactive protein and serum amyloid A. Some of the specific cytokines known to be involved in an acute inflammatory response include IL-1, TNF-$\alpha$ and IL-6. However, there are further pleiotropic effects of these cytokines, including induction of other interleukins, increased immunoglobulin synthesis, T- and B-cell proliferation and fever induction.

In general therefore, one will wish to include as part of the nucleic acid segment a promoter responsive to a species induced during the inflammation cascade, such as an acute phase protein gene promoter or a cytokine-responsive promoter such as one responsive to IL-1, IL-6 or TNF. Preferred acute phase protein gene promoters are complement factor 3 promoter or the serum amyloid A3 promoter. Of course other acute phase protein gene promoters could be used, including C-reactive protein, fibrinogen, serum amyloid protein, orosomucoid, alpha$^1$-antiprotease (antitrypsin) and other isoforms of SAA.

Of the various cytokine-responsive promoters, those for acute phase protein (APP) genes are particularly preferred for regulating recombinant anti-cytokine production. In response to various inflammatory stimuli, transcription of APP genes may increase 1000-fold or more, generally in proportion to the severity of the inflammatory condition. Since intravenously-injected adenoviruses infect hepatocytes, the site of most endogenous APP synthesis, the inventors have exemplified the invention by using non-replicating adenoviral vectors to deliver two APP promoter-luciferase reporter constructs to the appropriate target cells in vivo. Both promoters were positively regulated by inflammatory stimuli yet each exhibited a specific response pattern. Cytokine-inducible promoters such as these form the basis for novel approaches to preventing and/or treating inflammation, as they are expected to allow the production of anti-inflammatory proteins in the host in direct proportion to the intensity of an individual's inflammatory response.

Using cytokine-inducible promoters to control the production of recombinant anti-inflammatory proteins in vivo will allow regulated synthesis of these proteins in response to a host's own inflammatory mediators. This approach will limit the severity of inflammation without interfering with the beneficial roles of cytokines in host defense and immunity because at some chosen point the inflammation cascade will be modified or interrupted, thus preventing damage arising from an overproduction of inflammatory mediators. As inflammation subsides, so will production of the recombinant anti-inflammatory protein. Prolonged immunosuppression is therefore unlikely to occur.

One may introduce the disclosed nucleic acid segments into a cell or host animal by any of several means, including vector transfection. Viral vectors may be used to infect cells with the recombinant DNA; certain adenoviral vectors have proved particularly useful. The inventors have found that replication defective adenoviral vectors are effective. Of course DNA segments need not be introduced into cells by a viral vector: direct transformation may be performed by electroporation, gene gun techniques, or DNA-liposome complexes, for example. DNA/liposome complexes have been used to introduce DNA encoding prostaglandin synthase into rabbits, with subsequent production of prostaglandin E2 and prostacyclin (Conary, 1994).

The anti-inflammatory protein gene may encode a cytokine antagonist protein, such as an IL-1 receptor antagonist, a soluble TNF receptor, interleukin 10, interleukin-4 adrenocorticotropic hormone (ACTH), or $\alpha$-MSH, or it may encode an antibacterial or antiviral protein.

Anticytokine molecules may act in several ways: for example to directly antagonize (neutralize) specific cytokines. Preferred targets would be TNF-$\alpha$ and IL-1$\beta$. Or one may use molecules that interfere with the production of more than one inflammatory cytokine; for example, ACTH (which induces endogenous glucocorticoid production), IL-10 (inhibits LPS-induced cytokine production in vitro and prevents endotoxic death in mice challenged with LPS), as well as other "global" anti-inflammatory proteins such as IL-4 or prostaglandin G/H synthase (which produces $PGE_2$ and prostacylin. Other choices may include molecules that interfere with the actions of cytokines on target tissues such as α-MSH (melanocyte stimulating hormone-a fragment of the ACTH molecule that is now known to have potent anti-inflammatory activity), or molecules that neutralize other inflammatory mediators, e.g., inhibitors of either activated proteases or clotting factors. The other major category is anti-bacterial proteins. Anti-endotoxin proteins such as bactericidal permeability-increasing protein (BPI) are examples, but other antibacterial peptides may be useful as well.

The invention also encompasses methods of inducing expression of a protein in a cell where the expression of the protein is regulated or controlled by a promoter responsive to levels of cytokines in the cell. One obtains an appropriate vector that includes the gene for a selected protein such that the gene is under the transcriptional control of a cytokine-responsive promoter. Suitable cytokine-responsive promoters have been previously disclosed herein. Virtually any protein may be included in the vector; for example, a reporter molecule such as alkaline phosphatase, β-galactosidase, luciferase, etc might be desired to assess expression in response to agents that affect the promoter. In preferred practice, and where one desires in vivo control or regulation of cytokine production, one will include a cytokine-antagonist cDNA such as that for IL-1ra, or a cDNA for an antibacterial protein such as BPI.

The vector is introduced into a host cell by any of a number of procedures known to those skilled in the art, such as direct introduction of DNA by gene gun techniques or liposomal transfection, direct injection by intravenous, intramuscular or subcutaneous administration, for example, or by inhalation, or other forms of mucosal administration. Alternatively, the vector may be introduced into a subject's cells ex vivo and then the transfected cells may be implanted back into the subject.

Contacting the cell with a cytokine induces expression of the protein. In in vitro systems cytokine may be added to the culture media whereas in vivo one can challenge the host with a cytokine-inducing compound. An alternative to induced host challenge is to allow the protein expression to be regulated by any cytokine generated in the host caused by natural exposure to environmental hazards, such as airborne toxins, that induce cytokine production.

A wide range of cell types may be transformed with the disclosed vectors, including epithelial, endothelial, somatic and stem cells. Particular examples include lung, muscle, hepatic, etc. When adenoviral vectors are employed for transfection in an animal, hepatic cells are the preferentially targeted, cut cells in other organs are also infected.

The present invention may also be described in certain embodiments as a method of in vivo regulation of acute phase protein expression, comprising preparing an expression vector that includes a regulatory DNA segment encoding a cytokine inducible promoter in transcriptional control of a DNA encoding an anti-inflammatory protein and introducing the vector into an animal. In a preferred practice, the regulatory segment encodes complement factor 3 promoter or serum amyloid A3 promoter. These promoters are activated, presumably in response to serum amyloid or complement factor 3 induced by administration of compounds that induce an inflammatory response. The anti-inflammatory protein may be an inhibitor of cytokine production, or it may directly inactivate the cytokine, for example by binding with it, or it may inhibit the actions of the cytokine on target cells.

In particular applications, the disclosed methods are envisioned as useful for regulating cytokine response in an animal that has or is susceptible to systemic inflammation. This condition may arise from autoimmune diseases such as Sjogren's syndrome, systemic lupus erythematosus, Scleroderma, Grave's disease, multiple sclerosis or rheumatoid arthritis. An important application is potential use in organ transplant patients to alleviate the severity of rejection and at least reduce the need for high doses of immunosuppressants or systemic immunosuppression.

Other causative agents of inflammation are allergens and toxins, while in some diseases the causative agent has not been identified, such as in Kawasaki disease which is an idiopathic vasculitis associated with systemic inflammation (Sundel, et al. 1992). A particular example is the adverse reaction to bacterial endotoxin such as LPS (lipopolysaccharide) that may result in septic shock.

It is also contemplated that the disclosed methods may be useful in treating malignancies of plasma cells, such as multiple myeloma. IL-6 has been implicated in this disease (Klein, et al, 1995); thus, control by providing an in vivo regulated IL-6 antagonist may be beneficial.

The disclosed methods may thus be used for treatment of these conditions by administering to subjects in need of such treatment the recombinant gene vectors herein described. Generally, one will employ a vector that includes a cytokine antagonist; for example, IL-1 receptor antagonist (IL-1Ra) or soluble cytokine receptors that bind to the cytokine to neutralize its activity. Examples of soluble cytokine receptors include IL-7, IFN-γ, TNF-α, TNF-β and LIF. Additionally, other cytokine-binding proteins have been identified in viruses (Kuby in Immunology, second ed., Freeman and Co., NY, 1994, p 310) and would also be expected to be useful.

Of course one need not employ a cytokine-binding protein as the anti-inflammatory protein. The cytokines are thought to be at the top of the complex cascade of events resulting in an inflammatory response. There are therefore many points in the network of events at which control or regulation could be initiated. To do so, one selects a promoter responsive to a selected protein induced in the pathway. Potential anti-inflammatory proteins include, but are not limited to IL-1 receptor antagonist, soluble TNF receptors, IL-10, IL-4, ACTH, protease inhibitors, prostaglandin synthase, and endotoxin-neutralizing proteins such as bactericidal-permeability increasing protein.

The invention is not limited to the use of vectors that respond by producing a single antidote protein in response to inflammation. For example, multiple constructs may be administered, each producing a different protein; alternatively, multiple constructs may be combined in a single vector to produce several proteins or fused proteins that may or may not be engineered with cleavage sites to provide individual proteins in vivo.

In a particular embodiment, the invention includes an assay for detecting interleukin-6 in an animal. A vector that includes a reporter gene such as luciferase positioned under the transcriptional control of factor 3 or serum amyloid A3 promoter gene is introduced into the animal. The animal is then challenged to produce an inflammatory response, usually by administration of bacterial endotoxin. Measurement of hepatic luciferase activity is indicative of cytokines, e.g., IL-6, produced in response to the LPS challenge.

BRIEF DESCRIPTION OF THE DRAWINGS

FIG. 3A: Ad.CMV-Luc.
FIG. 3B: Ad.C3-Luc.
FIG. 3C: Ad.SAA3-Luc.

DETAILED DESCRIPTION OF PREFERRED EMBODIMENTS

Figure 1A:
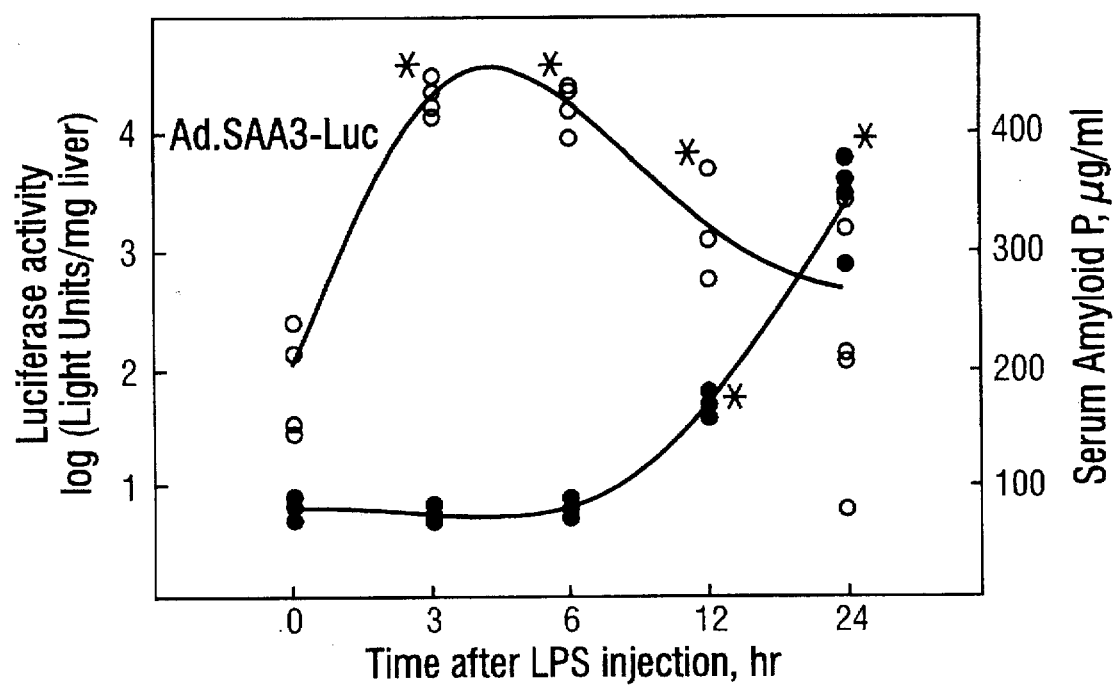
FIG. 1A. Time course of liver luciferase activity and serum amyloid P after injection of LPS. Each animal was infected with $10^9$ Ad.SAA3-Luc 3 days previously. After injecting 100 μg LPS i.p., samples of serum and liver were obtained at the indicated times ("0" time=5–10 min.). Luciferase activity—open circles, SAP concentration—closed circles. Each symbol represents one mouse. n=4–6 mice per group=significantly different from 0 time point (p<0.05). Note log scale on left ordinate.

The present invention arises from the discovery that protein expression can be regulated in vivo by an animal's own inflammatory mediators when a recombinant gene under the control of a cytokine inducible promoter is expressed in the animal. Hence, the present invention allows one to generate control of overactivation of the inflammatory response without interfering with the beneficial and necessary activity of the natural inflammatory reaction to infection or trauma.

The Acute Inflammatory Response

The acute phase response is a highly conserved, tightly controlled component of the host response to inflammatory stimuli. Numerous clinical data suggest that blood levels of certain acute phase proteins (e.g., C-reactive protein, serum amyloid A protein) usually increase in direct relationship to the severity of insults such as trauma, thermal injury, bacterial infection, or inflammatory diseases (Whicher et al., 1993). Critically injured patients are at particular risk for systemic inflammatory response that may be accompanied by progressive physiologic dysfunction of multiple organ systems, often involving organs not initially injured (Fitzsimmons, 1994). Acute phase inflammatory response may also be observed as a result of transplantation operations, apparently in response to allogeneic tissue (Ferrara, 1995).

The acute inflammatory response to infection or tissue injury is manifested as a complex cascade of nonspecific metabolic events, in which the duration and intensity of the inflammatory response must be regulated to prevent tissue damage and to allow tissue repair mechanisms to operate. This regulation may be provided by TGF-β, for example, a factor that facilitates fibroblast proliferation and deposition of the extracellular matrix required for tissue repair. Other agents involved in mediating the acute inflammatory response are IL-1, IL-6 and TNF-α. Locally, the effects of these cytokines are seen in increased adherence of circulating white blood cells to vascular endothelial cells and subsequent extravasation. IL-1 and TNF-α induce production of IL-8 by macrophages and increased expression of cell-adhesion molecules. Both IL-8 and IFN-γ are chemotactants, attracting neutrophils and macrophages, respectively, to adhere to endothelial cells. IFN-γ and TNF-β promote phagocytic activity of the neutrophils and macrophages to release lytic enzymes. The result of these localized reactions is a system-wide response that causes increased production of acute phase proteins by liver hepatocytes and increased production of corticosteroids due to the action of cytokines on the hypothalamus. Another possible effect is fever (Kuby, 1994).

It is contemplated that a variety of anti-cytokine proteins may be expressed from the inflammation-inducible promoters in the practice of the present invention. Such promoters would include but would not be limited to the promoters for serum amyoid A (Edrooke et al., 1989), C-reactive protein (Majello et al., 1990), fibrinogen (Fowlkes et al., 1984), $\alpha_1$-antitrypsin (Rangan & Das, 1990), $\alpha_2$-macroglobulin (Hattori et al., 1990), acid glycoprotein (Dewey et al., 1990) and the complement proteins (Colten, 1992).

Anti-cytokine proteins to be produced under the control of the listed promoters would include, but would not be limited to anti-cytokines such as the receptor or receptor antagonists for tumor necrosis factor (Graham and Prevec, 1991), lymphotoxin, IL-1, and chimeric proteins/antibody molecules. Direct antagonists include IL-1Ra, soluble TNFα receptors (Kolls, et al, 1994), and other proteins that bind to these or other inflammatory cytokines or to their receptors, thereby neutralizing cytokine action. Inhibitors of cytokine synthesis include ACTH, IL-10 and other proteins that inhibit inflammatory cytokine synthesis (Gérard, et al, 1993; Howard, et al, 1993; Gómez-Jiménez, et al, 1995). Other anti-cytokine proteins such as α-MSH inhibit cytokine action or may inhibit actions of inflammatory cytokines on their target cells (Watanabe, et al. 1993).

Certain anti-bacterial proteins are also expected to be useful when produced under the appropriate promoters. These include anti-endotoxins such as BPI (Marra, et al, 1990; Marra, et al, 1992; Ooi, et al, 1987; Rogy, et al, 1994; Evans, et al, 1995), active fragments of BPI, AOAH (Munford and Hall, 1986; Hagen, et al, 1991) and other endotoxin-neutralizing peptides. Other anti-bacterial proteins include defensins (Spitznagel, 1990; Lehrer, et al, 1991) and other peptides with bactericidal potency, including recombinant peptides (Piers, et al, 1994).

These proteins need not be limited to the specific peptide but may also be fused to other proteins as chimeric molecules, such as an antidote fused to other peptides that prolong half-life, target to particular cells or tissues, etc. (Peppel, et al, 1991).

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

One will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It may also be necessary to provide the recombinant protein with a heterologous leader/signal sequence to assure its secretion from the synthesizing cell into extracellular fluid, including plasma. This leader sequence, which is placed at the N-terminus of the precursor protein, may be modified experimentally to be sure that the native (correct) N-terminus results when the leader sequence is removed by proteolytic processing to yield the mature protein.

The critical boundaries of the two type-1 acute phase protein promoters used in the present examples, and cytokine-inducible expression using promoter-CAT plasmid constructs, have been demonstrated in vitro (Kawamura et al., 1992; Huang et al., 1990). In addition, the DNA sequences of the promoters are known to contain potential binding sites for known cytokine-induced transcription factors (Kawamura et al., 1992; Huang et al., 1990). Based on this information, these promoters were chosen to exemplify cytokine-regulated expression of recombinant proteins in vivo.

The complement factor 3 (C3) and serum amyloid A3 (SAA3) promoter were shown to increase recombinant protein expression in response to inflammatory stimuli in vivo. To deliver promoter-luciferase reporter constructs to the liver, where most endogenous amyloid P protein (APP) synthesis occurs, the APP promoter-luciferase constructs were introduced into a non-replicating adenoviral vector and injected intravenously into mice. When compared with the low levels of basal luciferase expression observed prior to inflammatory challenge, markedly increased expression from the C3 promoter was detected in liver in response to both lipolysaccharide (LPS) and turpentine, and lower-level inducible expression was also found in lung. In contrast, expression from the SAA3 promoter was found only in liver and was much more responsive to LPS than to turpentine. After LPS challenge, hepatic luciferase expression increased rapidly and in proportion to the LPS dose, reaching levels that were elevated 200-fold or more.

SAA3 promoter-regulated expression of luciferase contrasts with endogenous SAA3 mRNA expression, which is inducible in many tissues by LPS (Meek et al., 1986). The absence of extrahepatic expression by Ad.SAA3-Luc was not due to a failure of the adenoviruses to infect the other tissues, since constitutive expression was obtained in these tissues when Ad.CMV-Luc was used. No luciferase activity was observed in extrahepatic tissues infected with Ad.SAA3-Luc even when hepatic luciferase activity increased over 560-fold in the same animals in response to LPS. This finding, while not conclusive evidence that the SAA3 promoter is inactive in extrahepatic tissues, is in keeping with an important role for the region of this promoter (from −93 to −63) previously shown to limit its expression to liver-derived cells in vitro (Huang et al., 1990).

Transcription from the SAA3 promoter can be induced in vivo by intraperitoneal LPS but not by silver nitrate (Brissette et al., 1989) or casein (Meek et al., 1986), two other stimuli for eliciting acute phase responses in animals. The modest response of Ad.SAA3-Luc to turpentine, when compared to its response to LPS, is consistent with these results and suggests that the small (306 bp) region of the SAA3 promoter used in these studies probably contains elements that influence stimulus-specific transcription. IL-6 may play a minor role in stimulating this promoter, since LPS-induced SAA3 mRNA production was nearly normal in mice that lacked IL-6 due to interruption of its gene by targeted recombination (Kopf et al., 1994).

A striking feature of all the in vivo studies disclosed herein was the variability in the responses of individual animals to the same dose of LPS. To study the source of this variability, a number of other parameters were correlated with the level of luciferase expression. In general, the animals that had the highest hepatic luciferase levels appeared most ill (piloerection, diarrhea, weight loss). A direct correlation was also found between serum IL-6 concentrations and hepatic luciferase activity. Blood IL-6 levels have been reported to correlate with the intensity of the inflammatory response (Damas et al., 1992), suggesting that much of the observed heterogeneity in luciferase expression in these animals may be attributed to variability in the natural inflammatory response to LPS. This is further evidence that the recombinant promoters of the present invention would be under the control of the animal's own immune effectors.

Using cytokine-inducible promoters in gene transfer vectors therefore makes it possible to produce anti-inflammatory proteins in vivo in direct relationship to the intensity and duration of an individual's inflammatory response. By providing endogenously controlled production of recombinant anti-inflammatory proteins, the present compositions and methods are expected to limit the severity of the inflammatory response without interfering with the beneficial components of host defense and immunity.

While adenoviral vectors were used to demonstrate the invention, there are alternative methods for introducing the desired constructs into an animal. Some of these alternatives, as well as the use of viral vectors, are discussed.

Methods of DNA Transfection

Technology for introduction of DNA into cells is well-known to those of skill in the art. Exemplary general methods for delivering a gene into cells that have been described include chemical methods (Graham and VanDerEb, 1973); microinjection (Capecchi, 1980), electroporation (Wong and Neumann, 1982; Fromm et al., 1985) gene gun (Yang et al., 1990); viral vectors (Clapp, 1993; Danos and Heard, 1992; Eglitis and Anderson, 1988); receptor-mediated mechanisms (Wu et al., 1991; Curiel et al., 1991; Wagner et al., 1992); and injection of naked DNA (Fynan et al., 1993). Of course, in light of the technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effective amount of DNA to the epidermis (Fynan et al., 1993).

Liposomes and Nanoparticles

One vehicle that is contemplated for the present invention is a liposome gene delivery system. Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the vectors. They are widely suitable as both water- and lipid-soluble substances can be entrapped, i.e., in the aqueous spaces and within the bilayer itself, respectively. It is possible that nucleic acid bearing liposomes may even be employed for site-specific delivery of active agents by selectively modifying the liposomal formulation.

The formation and use of liposomes is generally known to those of skill in the art. For example, Couvreur et al. (1991; incorporated herein by reference) describe the use of liposomes and nanoparticles in the targeted antibiotic therapy of intracellular bacterial infections and diseases. Recently, liposomes were developed with improved serum stability and circulation half-times (Gabizon & Papahadjopoulos, 1988; Allen & Choun, 1987).

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention, particularly in the case of tissue specific promoters such as the SAA3 promoter, for example. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Adenoviral vectors

The adenovirus vectors of the present invention may be rendered replication defective through deletion of the viral early region 1 (E1A) region such that the virus is competent to replicate only in cells, such as human 293 cells, which express adenovirus early region 1 genes from their cellular genome. This is important because the virus will therefore not kill normal cells that do not express early gene products. Techniques for preparing replication defective adenoviruses are well known in the art as exemplified by Berkner et al., 1983, Ghosh-Choudhury et al., 1987, McGrory et al., 1988, and Gluzman et al., 1982.

Other than the requirement that the adenovirus vector be replication defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

In that the vectors of the present invention are replication defective, they will typically not have an adenovirus E1 region. Thus, it will be most convenient to introduce the promoter and anti-cytokine coding region at the position from which the E1 coding sequences have been removed. However, the position of insertion of the introduced material within the adenovirus sequences is not critical to the present invention. The transcription unit may also be inserted in lieu of the deleted E3 region in E3 replacement vectors as described previously by Karlsson et al. (1986).

It should also be pointed out that because the adenovirus vector employed is replication defective, it will not be capable of replicating in the cells that are ultimately infected. Moreover, it has been found that the genomic integration frequency of adenovirus is usually fairly low, typically on the order of about 1%. Thus, where continued treatment in certain individuals is required it may be necessary to reintroduce the virus every 6 months to a year. In these circumstances, it may therefore be necessary to conduct long term therapy.

The particular cell line used to propagate the recombinant adenoviruses of the present invention is not critical to the present invention. The recombinant adenovirus vectors can be propagated on, e.g., human 293 cells, or in other cell lines that are permissive for conditional replication-defective adenovirus infection, e.g., those which express adenovirus E1A gene products "in trans" so as to complement the defect in a conditional replication-defective vector. Further, the cells can be propagated either on plastic dishes or in suspension culture, in order to obtain virus stocks thereof.

Nucleic Acid Delivery

Initial efforts toward postnatal (somatic) gene therapy relied on indirect means of introducing genes into tissues, e.g., target cells were removed from the body, infected with viral vectors carrying recombinant genes, and implanted into the body. These types of techniques are generally referred to as ex vivo treatment protocols (Anderson et al., U.S. Pat. No. 5,399,346). Direct in vivo gene transfer has been achieved with formulations of DNA trapped in liposomes (Ledley et al., 1987); or in proteoliposomes that contain viral envelope receptor proteins (Nicolau et al., 1983); calcium phosphate-coprecipitated DNA (Benvenisty & Reshef, 1986); and DNA coupled to a polylysine-glycoprotein carrier complex (Wu & Wu, 1988). The use of recombinant replication-defective viral vectors to infect target cells in vivo has also been described (e.g., Seeger et al., 1984).

Wolff et al. demonstrated that direct injection of purified preparations of DNA and RNA into mouse skeletal muscle resulted in significant reporter gene expression (Wolfe et al., 1990). This was an unexpected finding, and the mechanism of gene transfer could not be defined. The authors speculated that muscle cells may be particularly suited to take up and express polynucleotides in vivo or that damage associated with DNA injection may allow transfection to occur.

Wolff et al. suggested several potential applications of the direct injection method, including (a) the treatment of heritable disorders of muscle, (b) the modification of non-muscle disorders through muscle tissue expression of therapeutic transgenes, (c) vaccine development, and (d) a reversible type of gene transfer, in which DNA is administered much like a conventional pharmaceutical treatment. In an elegant study Liu and coworkers showed that the direct injection method can be successfully applied to the problem of influenza vaccine development (Ulmer et al., 1993).

The use of gene transfer to synoviocytes as a means of treating arthritis has also been discussed (Bandara et al., 1992; Roessler et al., 1993). The protocols considered have included both the ex vivo treatment of isolated synoviocytes and their re-introduction into the animal and also direct gene transfer in which suitable vectors are injected into the joint. The transfer of marker genes into synoviocytes has already been demonstrated using both retroviral and adenoviral technology (Bandara et al., 1992; Roessler et al., 1993). In addition, U.S. Pat. No. 5,399,346 (incorporated herein by reference) discloses another ex vivo method of gene therapy in which foreign genes are introduced into cells by retroviral transfer and then those cells are re-introduced into a human subject.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. The preparation of genetic promoters with alterations in particular sequences such as effector binding sites is also routinely done with this technique.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

Pharmaceutical Compositions

In certain embodiments, the invention relates to pharmaceutical compositions wherein the adenovirus vector/anti-cytokine construct is dispersed in a pharmacologically acceptable solution or buffer. Preferred solutions include neutral saline solutions buffered with phosphate, lactate, Tris, and the like. Of course, one will desire to purify the vector sufficiently to render it essentially free of undesirable contaminants, such as defective interfering adenovirus particles or endotoxins and other pyrogens such that it will not cause any untoward reactions in the individual receiving the vector construct. A preferred means of purifying the adenoviral vectors involves the use of buoyant density gradients, such as cesium chloride gradient centrifugation.

It is contemplated that an effective amount of the vector construct will involve the administration of from about $5 \times 10^{10}$ to $5 \times 10^{12}$ virus particles, which may be given either as a single bolus injection or as an intravenous infusion over several hours.

In that adenovirus is a virus that infects humans, there may be certain individuals that have developed antibodies to certain adenovirus proteins. In these circumstances, it is possible that such individuals might develop an immunological reaction to the virus. Thus, where an immunological reaction is believed to be a possibility, one may desire to first test the subject to determine the existence of antibodies. Such a test could be performed in a variety of accepted manners, for example, through a simple skin test or through a test of the circulating blood levels of adenovirus-neutralizing antibodies. In fact, under such circumstances, one may desire to introduce a test dose of on the order of $1 \times 10^5$ to $1 \times 10^6$ or so virus particles. Then, if no untoward reaction is seen, the dose may be elevated over a period of time until the desired dosage is reached, such as through the administration of incremental dosages of approximately an order of magnitude.

The compositions used for administration will utilize pharmaceutically acceptable carrier. Suitable pharmaceutical carriers include, sterile aqueous solution, various organic solvents, emulsifying or suspending agents, or aqueous diluents such as water, ethanol, propylene glycol, glycerin or combinations thereof. Solutions will usually be formulated for administration by inoculation, e.g., intravenous, intraperitoneal or subcutaneously, prepared in accordance with conventional pharmaceutical practice, see, for example, "Remingtons Pharmaceutical Sciences" 15th Ed., pg. 1488–1501 (Mac Publishing Co., Easton Pa.).

Formulations will necessarily vary depending on the severity and location of the inflammation, the condition of the subject to be treated and so forth. The person responsible for treatment will determine the most suitable concentration for the individual subject. Preparations will preferably be in the form of a sterile aqueous solution containing, if desired, additional ingredients, for example, preservative, buffers, tenacity agents, antioxidants, stabilizers, non ionic wetting or clarifying agents, viscosity increasing agents and the like. Additionally, other beneficial compounds may be added, such as antipyretic agents or steroid hormones.

Suitable preservatives for use in such preparations include benzalkonium chloride, benzethonium chloride, chlorobutanol, thimerosal, and the like. Suitable buffers include boric acid, sodium and potassium bicarbonate, sodium and potassium borates, sodium and potassium carbonate, sodium acetate, sodium biphosphate and the like, in amounts sufficient to maintain the pH between about pH 6 and pH 8, preferably between about pH 7 and pH 7.5. Suitable tonicity agents are dextran 40, dextran 70, dextrose, glycerine, potassium chloride, propylene glycol, sodium chloride, and the like. Suitable antioxidant and stabilizers include sodium bisulfite, sodium metabisulfite, sodium thiosulfate, thiourea and the like. Suitable wetting and clarifying agents include polysorbate 80, polysorbate 20, poloxamer 282, and tyloxapol. Suitable viscosity increasing agents include dextran 40, dextran, 40, gelatin, glycerin, hydroxyethyl cellulose, hydroymethylpropyl cellulose, lanolin, methylcellulose, petrolatum, polyethylene glycol, polyvinyl alcohol, polyvinyl polyvinylpyrrolidone, carboxymethyl cellulose and the like.

MATERIALS AND METHODS

Cell lines and Media

HepG2 cells (ATCC HB 8065) were cultured in DMEM [Mediatech, Washington, D.C.] containing 10% heat-inactivated, low endotoxin fetal bovine serum (Hyclone, Logan, Utah), 2 mM glutamine, 50 I.U./ml penicillin, and 50 µg/ml streptomycin. When used to culture 293 cells (ATCC CRL 1573), the medium was further supplemented with 0.25 µg/ml amphotericin B (JRH Biosciences, Lenexa, Kans.). Cells were incubated at 37° C. and 5% $CO_2$. Cytokine-conditioned medium (CM) was prepared from the supernatants of adherent human peripheral blood monocytes incubated overnight in RPMI-1640 (Mediatech) containing 7% FBS, 1% human serum, 1 µg/ml *E. Coli* LCD25 LPS, and antibiotics and glutamine. Cells were removed by a brief centrifugation, and the supernatants were filtered (0.22 µm) and stored at −70° C. until needed. Adenovirus infection medium was DMEM supplemented with 2% heat-inactivated FBS. If not otherwise indicated, reagents were purchased from Sigma (St. Louis, Mo.).

C3 and SAA3 reporter constructs

Regulatory regions of the murine complement factor 3 (C3) and serum amyloid A3 (SAA3) promoters were amplified from mouse genomic DNA using PCR. The C3 promoter was amplified with oligonucleotide primers AGG ATC GAT AAT GCA ATG CCA AAT GTG (SEQ ID NO:1) and TTT TGG ATC CAA AAA GGT GGA AGG AAT GAA (SEQ ID NO:2) (UTSW Molecular Cardiology Oligonucleotide Synthesis Facility), flanking nucleotide positions −397 to +48 (Kawamura et al., 1992). The SAA3 promoter was amplified with oligonucleotide primers CTC ATC GAT ATC CCA TGA TTT ATC ACA C (SEQ ID NO:3) and TTT TGG ATC CGG GAC CCC AGG TGA GTG G (SEQ ID NO:4), flanking nucleotide positions −306 to +33 (Lowell et al., 1986). The resulting PCR products were cloned using the T/A cloning system of Invitrogen (San Diego, Calif.) to generate pCRII-C3 and pCRII-SAA3. The DNA sequences of both promoters were determined by M13 single-stranded sequencing using the Sequenase II sequencing system [US Biochemicals, Cleveland, Ohio]. The SAA3 promoter was subcloned as a NotI to BamHI fragment from pCRII-SAA3 into the polylinker upstream of luciferase in pBstLuc to generate pBstLuc-SAA3. Similarly, the C3 promoter was subcloned into the Not I and Spe I sites of pBstLuc to generate pBstLuc-C3. Firefly luciferase cDNA is downstream of a polycloning site so that one can introduce the promoter of interest directly upstream of luciferase.

Recombinant Adenoviruses

To make recombinant adenoviruses, the inserts from pBstLuc-C3 and pBstLuc-SAA3 were cloned as EcolCRI fragments into the SmaI site of pUC18 to obtain flanking SalI and Acc6561 sites. The inserts were then moved into the SalI and Acc651 sites of pAC.ESHRpl(−)(Gerard et al., 1995) to generate pAC-C3-Luc and pAC-SAA3-Luc. 293 cells (Graham et al., 1977) were then cotransfected with 10 μg of one of these plasmids and 5 μg of Xba I-digested viral DNA prepared from a recombinant adenovirus derived from Ad5dl309 (Gerard et al., 1995; Jones et al., 1979), using the calcium phosphate method and a glycerol shock to boost transfection efficiency. Homologous recombination between the pAC plasmid and the right 91% of the viral genome resulted in a recombinant viral genome of packagable size in which the C3-Luc or SAA3-Luc fusion gene replaced the native adenovirus early region 1. Recombinant adenoviruses were subjected to three cycles of plaque isolation and screening to insure purity. Ad.CMV-Luc (containing the CMV early promoter) was prepared as described (Herz et al., 1993), and Ad.No-Luc (promoterless luciferase) was also prepared.

Preparation of High Titer Recombinant Adenoviruses (Herz et al., 1993). Fifty confluent 150 mm plates of 293 cells were infected with recombinant adenovirus at an MOI of 0.01. When >90% of the cells showed cytopathic effects (5–7 days), cells were lysed with 0.1% NP-40 and the supernatant was clarified by centrifugation at 12,000×g for 10 min at 4° C. Virus was precipitated by the addition of 0.5 volumes of precipitation buffer (20% [w/v] PEG 8000, 2.5M NaCl) and incubation on ice for 60 minutes, then collected by centrifugation at 12,000×g for 20 minutes at 4° C. Virus was further purified by centrifugation on a discontinuous CsCl gradient (p=1.3, 1.4 gm/ml; 68,000×g, 20 min., 20° C.) and desalted on a Sepharose CL4B (Pharmacia) column equilibrated with isotonic saline buffer (10 mM Tris-HCl pH 7.4, 137 mM NaCl, 5 mM KCl, 1 mM $MgCl_2$). Following the addition of low-endotoxin BSA (10 μg/ml final concentration) to the eluted virus, aliquots were snap frozen and stored at −70° C. until used. The virus titer was then determined by plaque assay on 293 cell monolayers (Green, 1979).

Promoter Analysis in HepG2 cells

HepG2 cells from a freshly confluent 10 cm plate were distributed in six well plates ($2 \times 10^6$ cells/well) and incubated overnight. The following morning, the growth medium was replaced with 1 ml DMEM (2% FBS) containing a recombinant adenovirus (MOI=0.5–5), and incubation was continued for 90 minutes. The medium containing the virus was then aspirated, fresh growth medium was added, and the plates were returned to the incubator. Twenty-four hours later, cells were trypsinized in a total volume of 1.2 ml and split (500 μl per aliquot) into an equal volume of either whole growth medium or a 1:3 mixture of whole growth medium and cytokine-conditioned medium (1:6 final dilution of CM). Cells were harvested 18 hours later by incubating for 20 min at room temperature in 200 μl lysis buffer (PBS with 0.2% Triton X-100, 2.5 mM EDTA, 1 mM phenylmethylsulfonyl fluoride (PMSF), 0.5 μg/ml aprotinin, 0.5 μg/ml leupeptin), transferred to a microcentrifuge tube, and clarified by brief centrifugation. The clarified lysates were either assayed immediately or stored at −70° C. Two to four separate infections were performed per study. Studies were repeated at least once.

In Vivo Studies

Protocols for animal studies were approved by the UT-Southwestern Institutional Review Board for Animal Research. Specific pathogen-free, male ICR mice (Harlan, Indianapolis, Ind.) weighing 20–24 gm were housed in the institutional animal facility, fed standard mouse chow ad libitum, and used for studies within one week of arrival. Each mouse was injected via its tail vein with adenovirus diluted in 0.25 ml isotonic saline. Three days later, mice in different groups received saline (0.1 ml s.q.), steam distilled turpentine (0.1 ml s.q.), or E. coli 0127:B8 LPS (Sigma; in 0.2 ml i.p.). Eighteen to 24 hours later the mice were anesthetized (1 mg pentobarbital i.p.), bled from the retroorbital plexus, and euthanized by cervical dislocation. Organs were removed, weighed, and suspended in chilled lysis buffer as before. The ice-cold tissues were then homogenized with a Polytron (Tissue Tearer; Biospec Products, Bartlesville, Okla.) or by sonication (2 min, constant cycle, using a Sonifier 450 [Branson Ultrasonics, Danbury, Conn.]).

Assays

Luciferase activity was quantitated as described previously (Brasier et al., 1992). Briefly, 50 μl of cleared cell lysate or 5 μl of homogenized organ was added to assay buffer (25 mM glycylglycine, pH 7.8; 15 mM potassium phosphate, pH 7.8, 15 mM $MgSO_4$, 4 mM EGTA, 2 mM ATP, 1 mM DTT) to a total volume of 230 μl. Samples were transferred to an Optocomp II luminometer (MGM Instruments, Inc., Hamden, Conn.) and injected with 100 μl of luciferin solution (0.2 mM synthetic D-luciferin, 25 mM glycylglycine, pH 7.8; 10 mM DTT). Light emission at 32–550 nm was counted for 10 seconds. Background light emission from non-infected control cells was subtracted from the raw light units (ILU), and the results were normalized to protein concentration (Coomassie blue assay [Pierce]) or tissue weight. Serum amyloid P (SAP) protein was measured by rocket immunoelectrophoresis as described (Oldenburg et al., 1993; *Manual of Clinical Immunology*, 1980), using rabbit anti-SAP antiserum and 3 dilutions of commercial SAP (both from Calbiochem) as standards for each gel. Interleukin-6 was measured by an ELISA method (PerSeptive, Boston, Mass.).

Statistics

Differences between groups were analyzed using ANOVA (KWIKSTAT, Version 4, Texasoft, Dallas, Tex.). Differences with $p \leq 0.05$ were considered significant.

The following examples are intended to illustrate the practice of the present invention and are not intended to be limiting. Although the invention is here demonstrated with particular vectors that include certain promoters, other acute phase promoters could be used as well. Moreover, the antidote proteins that may be included in the vectors are numerous and may be selected in accordance with the desired methods of treatment and the medical conditions to be treated.

EXAMPLE 1

Cloning the murine C3 and SAA3 promoters

The regions of the complement factor 3 (C3) and serum amyloid A3 (SAA3) promoters responsible for induction of transcription in response to cytokines have been identified (Kawamura et al., 1992; Huang et al., 1990). These regions were cloned using standard PCR technology and their structure verified by DNA sequencing. The sequence of the C3 promoter clone was identical to that in the GeneBank database. The SAA3 promoter clone differed from the GeneBank sequence at four positions: a C to G transversion at nucleotide position −117; a T to A transversion at nucleotide position −121; and two single base pair deletions (−147 and −171). According to a Sites analysis on the isolated SAA3 sequence using the transcription factor database (TFD), none of these changes affected potential binding sites for factors known to regulate acute phase proteins.

Analysis of promoter activity in HepG3 cells

The reporter constructs were functionally characterized by infecting HepG2 cells (human hepatoma cells) with recombinant adenoviruses containing chimeric promoter-luciferase constructs and measuring luciferase activity before and after stimulation with cytokine-rich media (CM). No luciferase activity was detected in uninfected cells or in cells infected with an adenovirus containing a promoterless luciferase gene (Ad.No-Luc) (Li et al., 1994).

In contrast, cells infected with adenovirus containing the C3- or SAA3-luciferase constructs exhibited significant levels of induction (Table 1) by cytokine-rich media. Although the basal levels of luciferase activity in cells infected with these constructs were indistinguishable, activity in cells induced with CM was slightly higher in Ad.SAA3-Luc infected cells (19,790 ILU/µg protein) than in cells infected with Ad.C3-Luc (12,680 ILU/µg protein), resulting in greater induction for the SAA3-Luc construct (35-fold versus 26-fold).

The CMV promoter showed high basal expression and significant inducibility (Table 1) under the conditions used here. Induction from this promoter varied from 3- to 10-fold over a range of Ad.CMV-Luc concentrations (MOIs from 0.1 to 10), with optimal induction occurring at an MOI of 0.5 to 1.

TABLE 1

Induction of Luciferase Reporter Constructs with Cytokine-Conditioned Medium (CM)[a]

| Adenoviral construct | Luciferase activity (Light Units/µg cell protein)[b] | | Fold induction[c] |
| --- | --- | --- | --- |
| | Control medium | Cytokine-rich medium | |
| Ad.O-Luc | 2 | 5 | 3 |
| Ad.CMV-Luc | 2220 | 12680 | 6 |
| Ad.C3-Luc | 180 | 4610 | 26 |
| Ad.SAA3-Luc | 570 | 19790 | 35 |

[a]HepG2 cells were infected at an MOI of 5 and incubated for 24 hours. The infected cells were then trypsinized and split into normal growth medium (control) or a 1:5 mixture of whole growth medium and CM. The cells were harvested 18 hours later and luciferase activity was determined.
[b]The values represent the means of two infections in a representative study and are expressed as average ILU/µg protein.
[c]Fold-induction was calculated by dividing the average luciferase activity in cytokine-rich medium by the average activity in control medium.

EXAMPLE 2

Figure 1B:
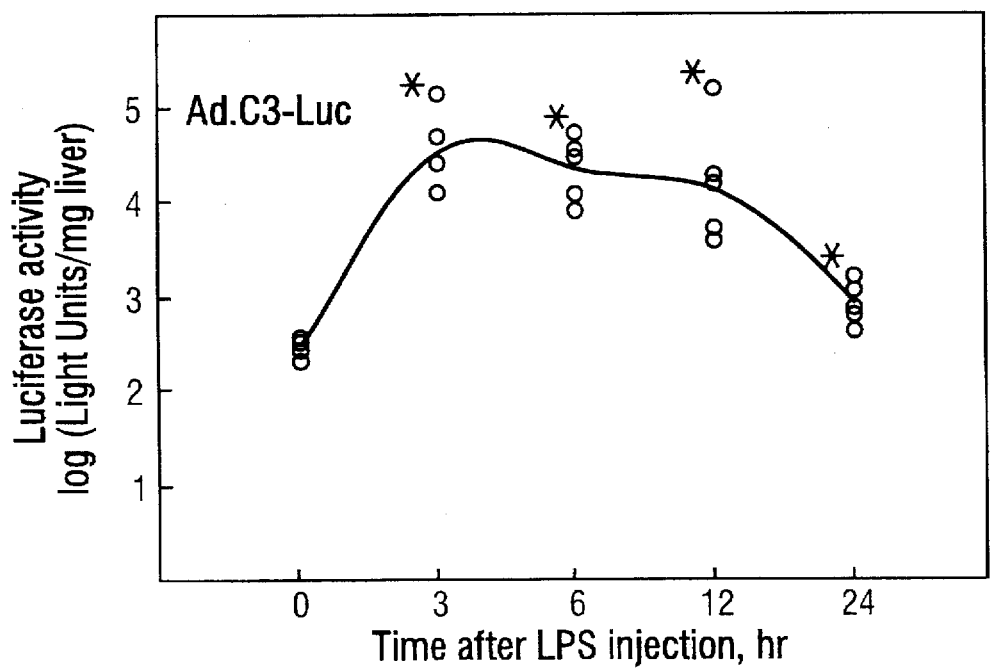
FIG. 1B. Time course as in FIG. 1A after infection with Ad.C3-Luc.

To determine if the cytokine induction observed in vitro could be achieved in vivo, mice were injected intravenously with various recombinant adenoviruses.
Analysis of promoter activity in mice Mice were injected using inoculi of $5 \times 10^8$ to $5 \times 10^9$ pfu. Three days later, the mice were challenged with saline, LPS, or turpentine, and 18–24 hrs later luciferase activity was measured in liver, spleen, heart, lung, and kidney. At high viral inocula ($>2 \times 10^9$), induction from the C3 promoter was not consistently demonstrated. Since it was known that recombinant adenoviruses can induce hepatitis (Yang et al., 1994), serum aminotransferase levels were measured in a sample of these mice. Significant elevations (ALT=465±191, AST 1310±820, n=14) above the levels were found in saline-injected control mice (ALT=48±6, AST=86±16, n=35). When lower viral inocula ($5 \times 10^8 - 1 \times 10^9$ were used, normal serum aminotransferase levels were observed and unequivocal induction of the C3 and SAA3 promoter constructs was demonstrable.
Time course of inducible luciferase expression FIG. 1A and FIG. 1B show the time course of hepatic luciferase expression from Ad.SAA3. Luc (FIG. 1A) and Ad.C3-Luc (FIG. 1B) after intraperitoneal LPS challenge. Luciferase expression from both constructs increased rapidly, remained at high levels (approximately 170-fold above baseline) for several hours, then gradually declined. Serum amyloid P levels, in contrast, increased slowly over the same time period (FIG. 1A) (Gershenwald et al., 1990). To exclude the possibility that the decrease in luciferase activity resulted from the loss of the virally transferred gene during the 24 hour observation period, a group of Ad.C3-Luc-infected mice was also injected with LPS at the end of the 24 hour period (i.e., at 4 days after viral infection); 3 hours later, log hepatic luciferase activity in these mice was 4.1 (S.D. 0.4, n=5), comparable to that seen at the 3 hr post-LPS time point one day earlier.

In the time-course study shown in FIG. 1A, luciferase expression began soon after LPS injection, plateaued (at about 180-fold above baseline) for several hours, then waned. This time course is very similar to that reported for LPS-induced transcription of the endogenous murine SAA3 gene (Lowell et al., 1986), suggesting that endogenous and adenovirus-mediated expression from the SAA3 promoter occur with similar rapidity. The descending arm of this curve is influenced, at least in part, by the short half-life of the firefly luciferase enzyme (Thompson et al., 1991); more stable reporters may demonstrate sustained expression in vivo.

In contrast, the CMV promoter was inducible by cytokine-rich media in vitro but expression decreased in vivo after animals were challenged with LPS. Although it is not certain that the response to LPS did not alter the stability or activity of luciferase, the increases in luciferase activity seen with the other promoters in LPS-challenged mice suggest that this is not the case. Rather, the data suggest that the activity of the CMV promoter decreases in hepatocytes following LPS stimulation, raising the possibility that this promoter can be inhibited by responses to other inflammatory agents as well. In contrast, dexamethasone administration was recently reported to enhance expression from this promoter in vivo (Malone et al., 1994). In light of this data, it is contemplated that the CMV promoter will also be useful in the practice of the present invention for the delivery of therapeutic proteins during inflammation (Kolls et al., 1994; Conary et al., 1994; Kobayashi et al., 1994).

EXAMPLE 3

Figure 2:
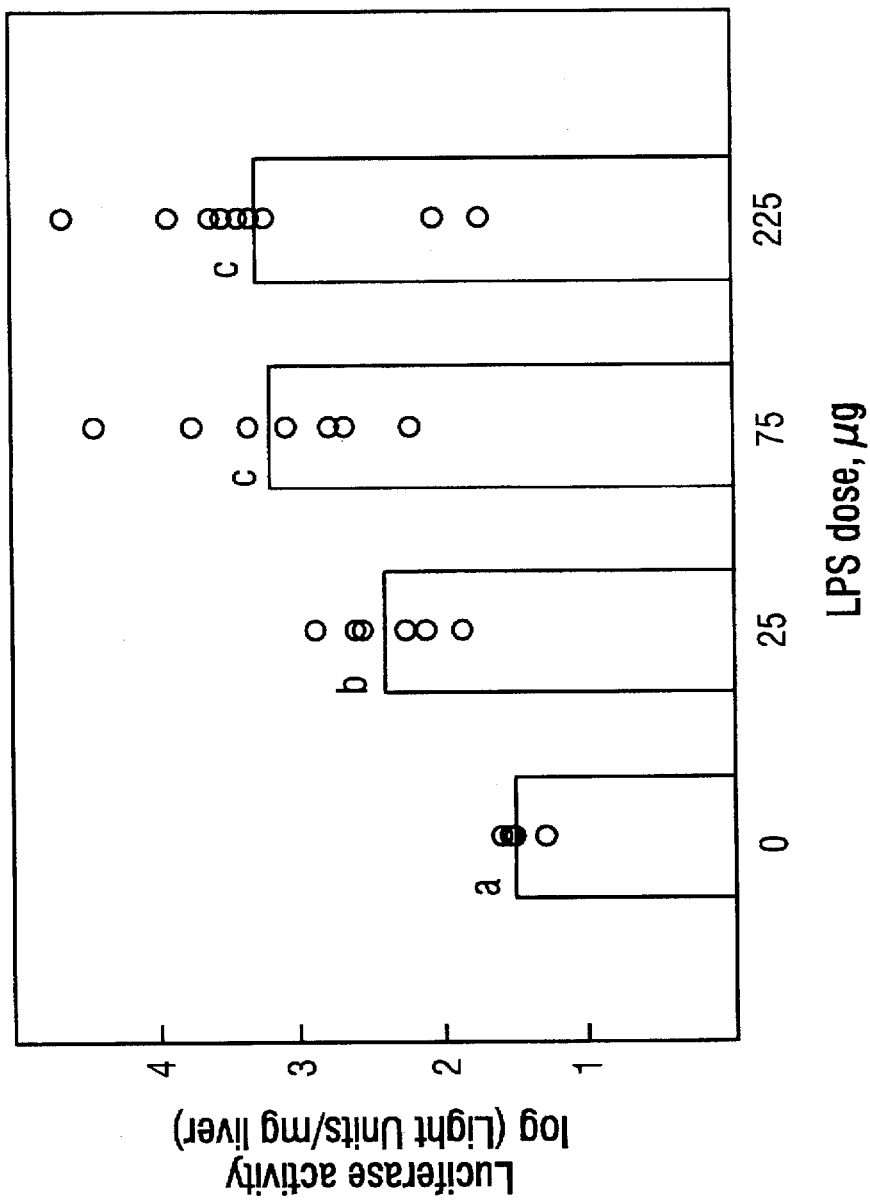
FIG. 2. Response of the SAA3 promoter to graded doses of LPS. Mice infected with Ad.SAA3-Luc were challenged i.p. 3 days later with saline or the indicated doses of LPS. Hepatic luciferase activity was measured after the animals were observed for 18 hours. Each open circle represents one mouse. Heights of bars indicate means; groups significantly different from others (p≦0.05) are indicated by letters (a,b,c) above bars.

Luciferase expression from the SAA3 promoter in response to increasing doses of LPS was measured.
Dose-dependent expression from the SAA3 promoter in vivo Mice were injected with Ad.SAA3-Luc ($7.5 \times 10^8$ pfu) and challenged three days later with saline or with 25, 75, or 225 µg of LPS. As shown in FIG. 2, there was a positive correlation between the LPS dose and the level of induction. Relative to saline-treated animals, mean luciferase activity was 10-, 170-, and 220-fold higher in mice receiving 25, 75, and 225 µg of LPS, respectively ($p<0.002$ for trend).

EXAMPLE 4

Figure 3A:
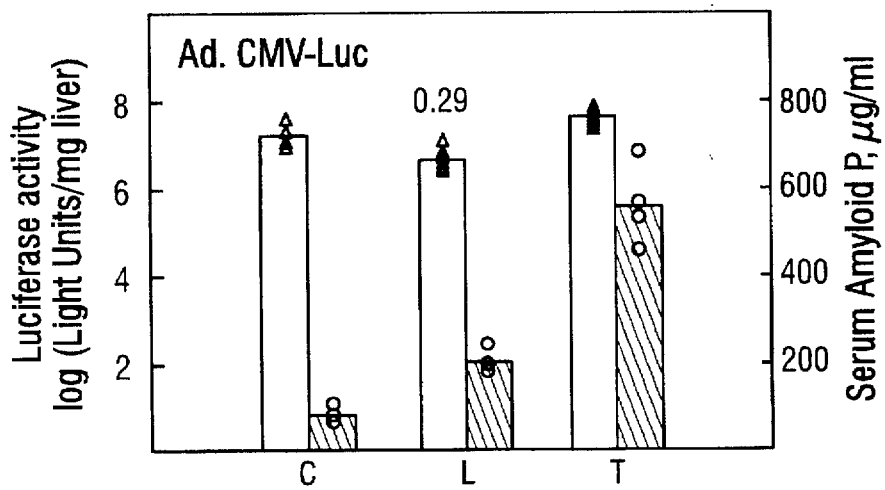
FIGS. 3A–3C. Responses of adenovirus-infected mice injected with saline (C), lipopolysaccharide (L), or turpentine (T). Each open symbol represents results from a single mouse; heights of bars indicate means; n=7 to 9 mice triangles: Open bars, unfilled triangles: luciferase activity in liver lysates. Note log scale on left ordinate. The numbers above groups indicate -fold increases that were significantly different from C (p<0.05). Stippled bars, open circles: serum amyloid P (SAP) levels in serum obtained from 4 or 5 mice in each group. Note linear scale on right ordinate. Each L and T group was different from C in each study (p<0.05). Mice in each group had been infected with approximately $1\times10^9$ adenoviral pfu 3 days before challenge.
Figure 3B:
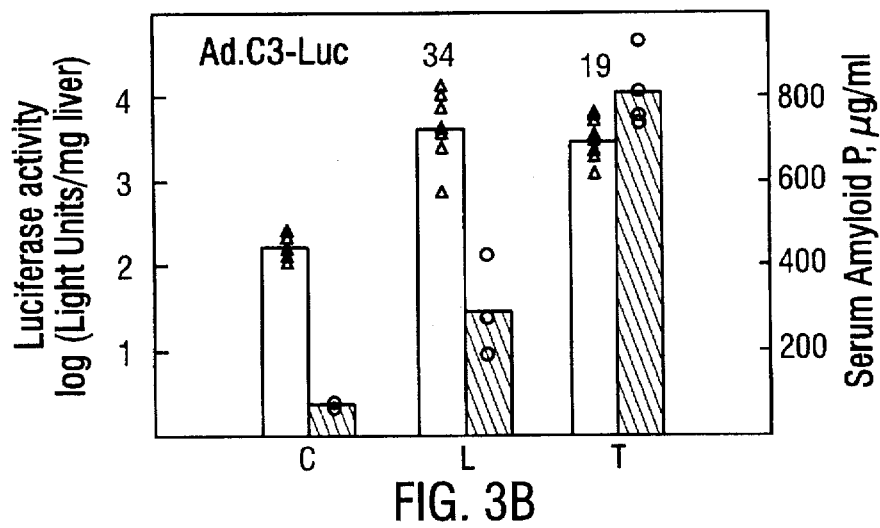
Figure 3C:
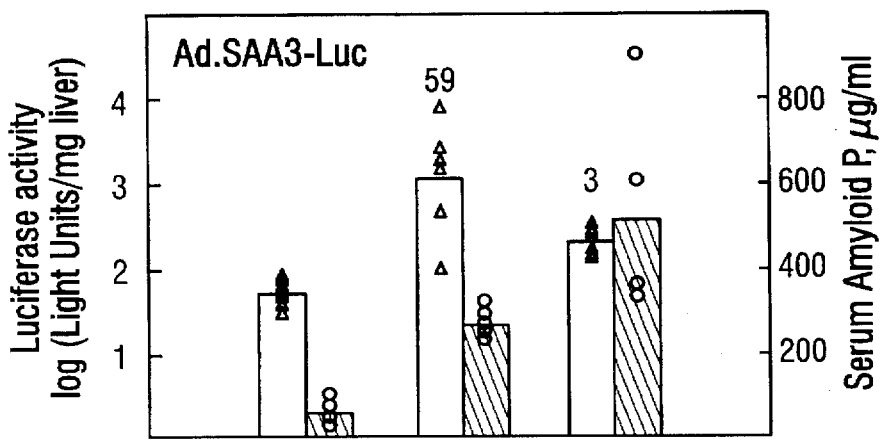

The response of both the endogenous SAP gene and the virally transferred genes was measured in the same animals.
Comparison of the SAA3 and C3 promoters in vivo Mice were euthanized at 18–20 hours after LPS injection (Pepys et al., 1979). As shown in FIG. 3, basal expression from the CMV promoter was high ($10^6$ to $10^7$ ILU/mg liver), whereas basal expression from the C3 and SAA3 promoters was very low (approximately $10^2$ ILU/mg liver). Moreover, basal activity from the SAA3 promoter in vivo was less than that from the C3 promoter: in two studies using similar viral doses ($5 \times 10^8$ pfu), basal expression from the C3 promoter averaged 250 ILU/mg liver (S.D.=125, n=15) while expression from the SAA3 promoter averaged 50 ILU/mg liver (S.D.=17, n=11; p=<0.001).

The SAA3 and C3 promoters were both inducible by inflammatory stimuli in vivo. When challenged with LPS 18–20 hours earlier, mice infected with Ad.SAA3-Luc had mean liver luciferase activities that were 59-fold greater than those found in saline challenged controls. When challenged with turpentine, however, luciferase expression from Ad.SAA3-Luc was only 3-fold above baseline levels.

In contrast, in mice infected with Ad.C3-Luc, liver luciferase activities increased an average of 29-fold in response to 100 µg LPS (range: 24- to 34-fold, 2 studies) and 12-fold in response to turpentine (range: 6- to 19-fold, 3 studies). Paradoxically, expression from the CMV promoter, which had been stimulated by cytokine-rich medium in vitro, decreased 3-fold in response to LPS in vivo. Serum amyloid P levels, measured in the same mice, confirmed that an acute phase response occurred in mice with either turpentine or LPS challenge (FIG. 3). In addition, body weight decreased 5–8% overnight in mice that received turpentine (Oldenburg et al., 1993) or LPS while increasing 5% in saline-injected mice.

To exclude the possibility that the Ad.SAA3-Luc response to turpentine was greater at earlier time points, Ad.SAA3-Luc-infected mice were challenged with saline, 100 µg LPS, or turpentine and liver luciferase activity was measured 6 hours later. When compared to the saline-treated animals, mice that received LPS averaged 800-fold greater activity while those that received turpentine showed no elevation. In another control study, no luciferase activity above background was detectable in the livers of uninfected mice or mice infected with $2 \times 10^9$ Ad.No-Luc (promoterless luciferase) and then challenged with LPS or turpentine.

Although adenoviral vectors principally target the liver, expression of recombinant proteins delivered by these vectors has been demonstrated in other tissues (Herz et al., 1993). Luciferase activities were determined in homogenates of spleen, kidney, heart and lung from mice that had been infected with the different adenoviral constructs. Luciferase expression from the constitutive CMV early promoter occurred in each of these tissues. In contrast, no activity was detected from the SAA3 promoter in any tissue other than liver. Expression from the C3 promoter was detected in liver and lung, but not in kidney, heart or spleen. In lung, expression from the C3 promoter was low (115±73 ILU/mg tissue) but inducible by turpentine and LPS (mean= 4-fold increase, three studies, each significant at p<0.05). The time course in lung paralleled that for liver shown in FIG. 1B. Expression from the CMV promoter in non-hepatic tissues was not altered by inflammatory stimuli.

EXAMPLE 5

A striking feature of the in vivo studies was the variability in luciferase expression found within each group among the mice that received LPS.

Serum interleukin-6 levels

Figure 4:
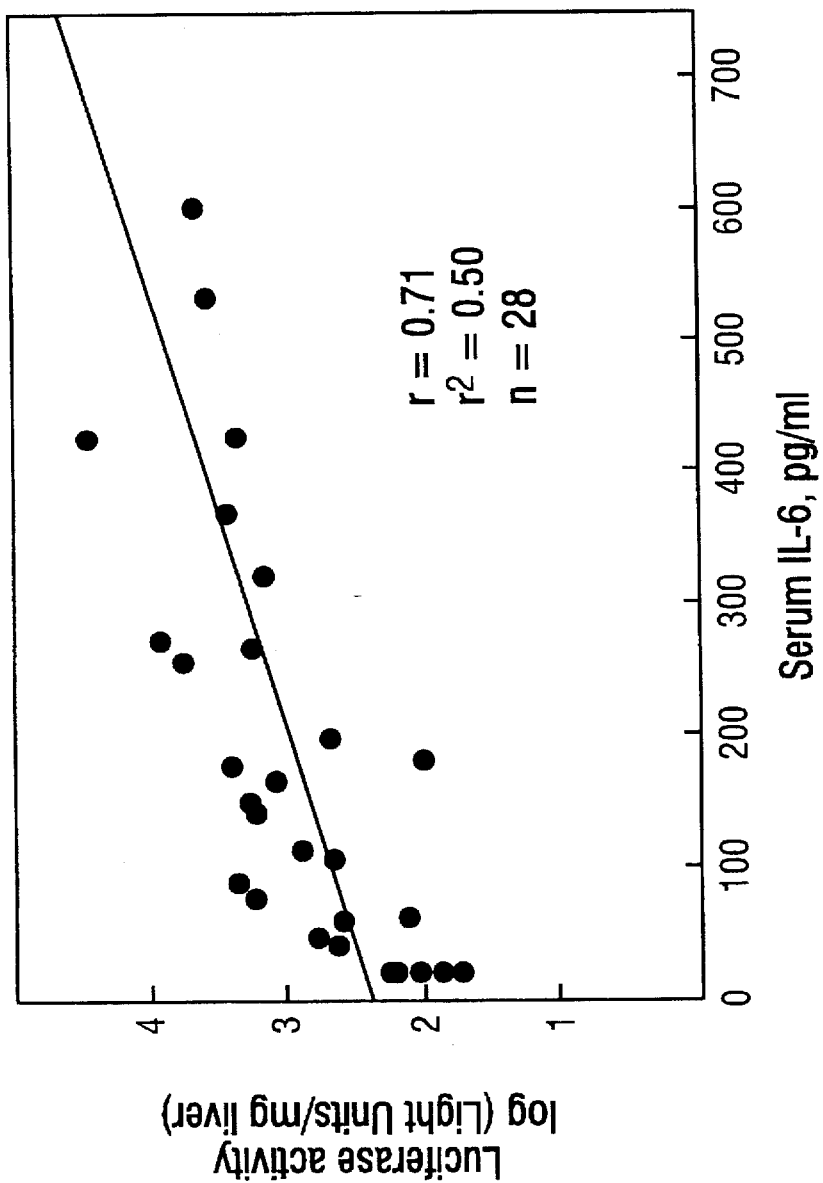
FIG. 4. Relationship between liver luciferase activity and serum interleukin-6 concentration. Each animal (cloned circle) had been injected with Ad.SAA3-Luc 4 days previously and had received an LPS injection 18–20 hrs before liver and serum samples were obtained. Different animals received different LPS doses (see FIG. 2 and FIG. 3).

To test the hypothesis that this variability resulted from heterogeneity in the host response to LPS, the concentration of interleukin-6 (IL-6) was measured in serum obtained (immediately prior to euthanasia) from animals injected with Ad.SAAC.Luc. There was a positive correlation between individual serum IL-6 levels and hepatic luciferase expression (FIG. 4; p<0.001).

EXAMPLE 6

The utility of the disclosed methods to control in vivo expression of a recombinant protein has been illustrated in Example 2. It is evident that numerous conditions would be amenable to treatment using these same methods, as illustrated in the following exemplary protocols.

The exemplary protocols relating to sepsis and multiple myeloma are examples of treatments for systemic disorders. Local inflammatory conditions are exemplified by problems encountered in organ transplantation. Other local inflammations that might be treated by these methods include arthritis (rheumatoid) where treatment might be effected by direct injection of the appropriate antidote protein (e.g., IL-4) vector into the affected joint (Roessler, et al, 1993). One method of administration would be to use liposome/DNA complexes or alternatively, an adenoviral vector method as described previously.

Treatment or Prevention of Severe Sepsis and Septic Shock

Major trauma is often fatal, not because of the initial insult but because of complications arising within the first few days of the trauma. If such a patient becomes infected, the normal body response is to produce cytokines; however, as cytokine levels increase, acute respiratory distress syndrome (ARDS), renal failure, or shock may develop. To control the overproduction of cytokines, one would administer a gene delivery vector encoding a selected antidote protein. Patients could be treated who show early signs of sepsis, or even severe sepsis; however, in some cases of individuals at high risk for sepsis, prophylactic treatment may be advisable.

Gene delivery vectors may be constructed from a non-replicating adenovirus ($6 \times 10^{12}$ plaque-forming units) or a DNA-liposome complex (10 mg DNA). The encoded antidote protein may be any of TNF-receptor-human immunoglobulin fusion protein, IL-10, fibrinogen, ACTH, or BPI. To provide multiple recombinant antidote proteins in vivo, more than one kind of vector-antidote protein may be given to a patient.

To prevent sepsis, for example, each vector-construct will be administered once, intravenously, on the third or fourth day after injury. This is a crucial period, as the acute phase response to trauma subsides normally 3 days after injury (Boralessa, et al,1986; Mustard, et al, 1987; Miholic, et al, 1986). Failure of acute phase response to subside frequently points to complications triggered by infection. This is the point at which antidote protein therapy would be initiated, by controlling protein production using acute phase protein promoters. When the inflammatory response subsides, so will production of the antidote protein(s).

Multiple Myeloma

Multiple myeloma is a malignancy of plasma cells, the blood cells that produce antibodies. Recent studies implicate IL-6 in the pathogenesis of multiple myeloma, and antibodies to IL-6 have produced amelioration of the disease in some patients (Klein, et al, 1995).

Gene therapy that produces an IL-6 antagonist in response to IL-6 would be the basis of a treatment employing administration of a vector with an IL-6 responsive promoter positioned upstream of an IL-6 antagonist protein. One would select any of several acute phase protein promoters, including those from the CRP, fibrinogen or C3 genes. A choice of IL-6 antagonist for example would include antibodies to IL-6, or a modified IL-6 that functions as a receptor antagonist (Savino, et al, 1994).

Prevention of Renal Transplant Rejection

Patients with chronic renal failure in some cases will be transplanted with a donor kidney. Rejection of the nonhomologous organ may be a problem. The disclosed methods offer a mode of preventing severe rejection.

A vector constructed as herein disclosed will be employed. Modifications may include delivery systems that particularly target the renal artery of the donor kidney, i.e., the cells in the arterial vessel wall. Possible constructs would include promoters for IL-1, IL-1Ra, IL-6, IL-8, or TNFα. These appear to be preferred over acute phase protein promoters, taking into consideration they may be more responsive when delivered to vessel wall cells. Potential anti-cytokine proteins might include, but not be limited to, soluble TNF receptors, IL-1Ra, IL-10, IL-4, etc.

Each vector-construct will be introduced into the donor kidney prior to transplant into the recipient. After allowing the vector to enter vessel wall cells, the renal vessels will be flushed with physiological fluid to remove unattached vector, thereby delivering the DNA only to the kidney.

It is expected that when kidney rejection begins, local cytokine production would increase synthesis of anti-cytokine protein. The antidote protein would limit the severity of rejection and reduce the need for systemic immunosuppression. In some cases, one might combine the cytokine-inducible vector with a vector that constitutively produces anti-inflammatory protein(s). This would produce chronic (constitutive) local immunosuppression in the kidney yet allow increased (inducible) immunosuppression should rejection ensue.

EXAMPLE 7
Human Gene Transfer Protocols

This example describes some of the ways in which the present invention is envisioned to be of use in the treatment of human disorders via gene therapy, such as, for example, in the treatment of systemic inflammatory response or arthritic disease.

Human subjects for whom the medical indication for adenovirus-mediated gene transfer has been established would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus expressing the anti-cytokine protein under control of the cytokine regulated promoter is prepared and purified by any method that would be acceptable to the Food and Drug Administration for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized during the trial for at least 48 hrs. to monitor acute and delayed adverse reactions. Serum cholesterol levels and liver function parameters would be monitored twice daily to follow the efficacy of the gene transfer and to test for possible adverse hepatic inflammatory reactions (a potential side effect).

Further possible follow-up examinations include obtaining of a liver biopsy in which the pattern of expression of the transferred gene could be directly assessed and measuring the blood level of the antidote protein. This would also supply information about the number of hepatocytes that have taken up the transferred gene and about the relative promoter strength in the human liver. Based on the data obtained adjustments to the treatment may be desirable.

REFERENCES

The references listed below are incorporated herein by reference to the extent that they supplement, explain, provide a background for or teach methodology, techniques and/or compositions employed herein.

Alcorn et al., *Mol. Endocrinol.*, 7:1072–1085, 1993.
Allen and Choun, *FEBS Lett.*, 223:42–46, 1987.
Anderson et al., U.S. Pat. No. 5,399,346.
Baumann and Gauldie, *Immunology Today*, 15:74–80, 1994.
Boralessa et al., *Anaesthesia*, 41:11–15, 1986.
Brasier and Ron, *Methods Enzymol.*, 216:386–414, 1992.
Brissette et al., *J. Biol. Chem.*, 264:19327–19332, 1989.
Casey, L. C. *Ann. Thorac. Surg.*, 56:S92–96.
Ciliberto et al., *EMBO J.*, 6:4017–4022.
Cioffi, W. G., Burleson, D. G., Pruitt, Jr., B. A. *Arch. Surg.* 128:1260–1267.
Cohen, "Naked DNA Points Way to Vaccines," *Science*, 259:1691 1692, 1993.
Colten, H. R., *J. Appl. Physiol.* 72, 1–7, 1992.
Conary et al., *J. Clin. Invest.*, 93:1834–1840, 1994.
Couvreur et al., *Pharm. Res.*, 8:1079–1086, 1991.
Couvreur, Crit. *Rev. Ther. Drug Carrier Syst.*, 5:1–20, 1988.
Couvreur et al., U.S. Pat. No. 4,489,555, 1984.
Couvreur et al., *FEBS Lett.*, 84:323–326, 1977.
Cox et al., *J. Virol.* 67(9):5664–5667, 1993.
Damas et al., *Ann. Surg.*, 215(4):356–362, 1992.
Dewey, M. J., Rheaume, C., Berger, F. G. and Baumann, H., *J. Immunol.* 144, 4392–4398, 1990.
Düzgünes et al., *Antimicrob. Agents Chemother.*, 32:1404–1411, 1988.
Evans et al., *J. Infect. Dis.*, 171:153–160, 1995.
Fattori, E. et al., *J. Exp. Med.*, 180:1243–1250.
Ferrara, J. L. *Curr. Opin. Oncol.*, 6:127–34.
Fitzsimmons, L. *Crit. Care Nurs. Q.*, 17:74–90.
Fowlkes, D. M., Mullis, N. T., Comeau, C. M. and Crabtree, G. R., *Proc. Natl. Acad. Sci. USA* 81, 2313–2316, 1984.
Fynan et al., "DNA vaccines: Protective immunizations by parenteral, mucosal, and gene-gun inoculations," *Proc. Natl. Acad. Sci. USA*, 90:11478–11482, 1993.
Gabizon and Papahadjopoulos, *Proc. Natl. Acad. Sci. USA*, 85:6949–6953, 1988.
Gerard and Meidell, in DNA Cloning: A Practical Approach, eds. Hames, B. D. & Glover, D. M. (Oxford University Press, Oxford and New York), 1995.
Gerard et al., *J. Exp. Med.*, 177:547–550, 1993.
Gershenwald et al., *Proc. Natl. Acad. Sci. USA*, 87:4966–4970, 1990.
Ghosh-Choudhury, G. and Graham, F. L. (1987) *Biochem. Biophys. Res. Comm.*, 147, 964–973
Gluzman, Y., Reichl, H., and Solnick, D. (1982) in *Eukaryotic Viral Vectors* (Gluzman, Y., ed) pp. 187–192, Cold Spring Harbor Press, Cold Spring Harbor, N.Y.
Gomez-Jimenez et al., *J. Infect. Dis.*, 171:472–475, 1995.
Graham et al., *J. Gen. Virol.*, 36:59–72, 1977.
Green, *Meth. Enzymol.*, 58:425–435, 1979.
Hagen et al., *Biochemistry*, 30:8415–8423, 1991.
Hattori, M., Abraham, L. J., Northemann, W. and Fey, G. H. *Proc. Natl. Acad. Sci. USA* 87, 2364–2368, 1990.
Hayashi et al., *J. Biol. Chem.*, 269:23872–23875, 1994.
Herz and Gerard, *Proc. Natl. Acad. Sci. USA*, 90:2812–2816, 1993.
Howard et al., *J. Exp. Med.*, 177:1205–1208, 1993.
Huang et al., *Mol. Cell Biol.*, 10:3619–3625, 1990.
Jones and Shenk, *Cell*, 17:683–689, 1979.
Kawamura et al., *Biochem. J.*, 283:705–712, 1992.
Klein, et al., *Blood*, 85:863–872, 1995.
Kobayashi et al., *Nucleic Acids Res.*, 22:4470–4476, 1994.
Koss et al., *J. Infect. Dis.*, In press.
Kolls et al., *J. Infect. Dis.*, 171:570–575, 1995.

Kolls et al., *Proc. Natl. Acad. Sci. USA*, 91:215–219, 1994.
Kopf et al., *Nature*, 368:339–342, 1994.
Lehrer et al., *Cell*, 64:229–230, 1991.
Li et al., *Gene*, 138:257–258, 1994.
Li et al., *J. Biol. Chem.*, 265:4136–4142.
Lowell et al., *J. Biol. Chem.*, 261:8453–8461, 1986.
Lowell et al., *J. Biol. Chem.*, 261:8442–8452, 1986.
Lynn et al., *Clin. Infect. Dis.*, 20:143–158, 1995.
Majello, B., Arcone, R., Toniatti, C. and Ciliberto, G. *EMBO J.* 9, 457–465, 1990).
Malone et al., *J. Biol. Chem.*, 269:29903–29907, 1994.
Manual of Clinical Immunology (*American Society for Microbiology*, Washington, D.C.), p. 116–120, 1980.
Marra et al., *J. Immunol.*, 148:532–537, 1992.
Marra et al. *J. Immunol.*, 144:662–666, 1990.
McGrory, W. J., Bautista, D. S., and Graham, F. L. (1988) *Virol.*, 163, 614–617
McPhaul et al., *J. Biol. Chem.*, 268:26063–26066, 1993.
Meek and Benditt, *J. Exp. Med.*, 164:2006–2017, 1986.
Miholic et al., *Ann. Thor. Surg.*, 42:429–433, 1986.
Miossec, P., Chomarat, P., Dechanet, J. et al. Interleukin-4 inhibits bone resorption through an effect on osteoclasts and proinflammatory cytokines in an ex vivo model of bone resorption in rheumatoid arthritis. *Arthritis Rheum.* 1994;37:1715–1722.
Munford et al., *Science*, 234:203–205, 1986.
Mustard et al., *Arch. Surg.*, 122:69–73, 1987.
Oldenburg et al., *Eur. J. Immunol.*, 23:1889–1894, 1993.
Ooi et al., *J. Biol. Chem.*, 262:14891–14894, 1987.
Peppel et al., *J. Exp. Med.*, 174:1483–1489.
Pepys et al., *Nature*, 278:259–261, 1979.
Piers et al., *Antimicrob. Agents Chemother.*, 38:2311–2316.
Ramani, M., Ollivier, V., Ternisien, C. et al., Interleukin 4 prevents the induction of tissue factor mRNA in human monocytes in response to LPS or PMA stimulation. *Br. J. Haematol.* 1993; 85:462–468.
Rangan, V. S. & Das, G. C. *J. Biol. Chem.* 265, 8874–8879, 1990.
Roessler, B. J., et al, *J. Clin. Invest.* 1993:1085–1092.
Rogy et al., *J. Clin. Immunol.*, 14:120–133, 1994.
Savino, R., et al, *EMBO J.* 13:5863–5870, 1994.
Spitznagel, J. D., *J. Clin. Invest.*, 86:1381–1386, 1990.
Sundel, R. P. et al., *Am. J. Otol.*, 13:512–515.
Suffredini, A. F., *Crit. Care Med.*, 22:S12–S18, 1994.
Tang et al., *Nature*, 356:152–154, 1992.
Te Velde, A. A., Huijbens, R. J. F., Heije, K., De Vries, J. E., Figdor, C. G. Interleukin-4(IL-4) inhibits secretion of IL-1β, tumor necrosis factor α, and IL-6 by human monocytes. *Blood.* 1990;76:1392–1397.
Thompson et al., *Gene*, 103:171–177, 1991.
Ulmer et al., "Heterologous Protection Against Influenza by Injection of DNA Encoding a Viral Protein," *Science*, 259:1745–1749, 1993.
van Oers et al., *Clin. Exp. Immunol.*, 71:314–319, 1988.
Wang et al., *Proc. Natl. Acad. Sci. USA*, 90:4156–4160, 1993.
Watanabe et al., *Brain Res. Bull.*, 32:311–314, 1993.
Whicher et al., *Acute Phase Proteins*, eds. Mackiewicz, A., Kushner, I. and Baumann, H. (CRC Press, Boca Raton), pp. 644–650.
Whitton et al., *J. Virol.* 67:(1)348–352,1993. Edrooke M. R., Burt, D. W., Cheshire, J. K. and Woo, P., *Mol. Cell. Biol.* 9, 1908–1916, 1989.
Yang et al., *Proc. Natl. Acad. Sci. USA*, 91:4407–4411, 1994.
Yoshimura et al., *Transplantation*, 51:172–176, 1991.

---

What is claimed is:

1. A method of providing inflammation responsive protein expression in a cell comprising the steps of:
   (a) introducing into a cell a vector that includes a selected protein gene under the transcriptional control of a heterologous inflammation responsive promoter; and
   (b) contacting said cell with a cytokine or inducing said cell to produce a cytokine wherein said cytokine activates the inflammation responsive promoter gene.

2. The method of claim 1, wherein the protein is a cytokine antagonist.

3. The method of claim 2, wherein said cytokine antagonist is IL-1ra, TNF-α receptor, IL-4, IL-10, ACTH, IFN-γ, TNF-β receptor, prostaglandin synthase or LIF receptor.

4. The method of claim 2 wherein the cytokine antagonist is soluble TNF receptor protein.

5. The method of claim 1, wherein said cytokine-responsive promoter is the SAA3 promoter.

6. The method of claim 1, wherein said cytokine-responsive promoter is the C3 promoter.

7. The method of claim 1, wherein said cell is in an animal.

8. The method of claim 1 wherein the cell is a hepatic cell.

9. The method of claim 1 wherein the vector is further defined as including at least two DNA segments encoding a protein under the control of a cytokine-inducible promoter.

10. The method of claim 1 further including providing at least two vectors encoding a protein under the control of a cytokine-inducible promoter.

\* \* \* \* \*